(12) United States Patent
Kontschieder et al.

(10) Patent No.: US 8,262,992 B2
(45) Date of Patent: Sep. 11, 2012

(54) MODULAR SENSOR CASSETTE

(75) Inventors: Heinz Kontschieder, Graz (AT); Marco Jean Pierre Leiner, Graz (AT); Wolfgang Huber, Lannach (AT); Franz-Josef Krysl, Graz (AT); Christoph Ritter, Graz (AT); Helmut Offenbacher, Graz (AT); Bernhard Schaffar, Graz (AT); Marie-Luise Schinnerl, Semriach (AT); Johann Harer, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 301 days.

(21) Appl. No.: 12/269,280

(22) Filed: Nov. 12, 2008

(65) Prior Publication Data
US 2009/0156966 A1 Jun. 18, 2009

Related U.S. Application Data

(60) Provisional application No. 60/987,446, filed on Nov. 13, 2007.

(51) Int. Cl.
*G01N 21/00* (2006.01)
(52) U.S. Cl. ......................................... 422/63
(58) Field of Classification Search .............. 422/58, 422/63, 554
See application file for complete search history.

(56) References Cited

U.S. PATENT DOCUMENTS

| | | | | |
|---|---|---|---|---|
| 4,727,033 A | * | 2/1988 | Hijikata et al. ............. | 436/69 |
| 4,849,177 A | * | 7/1989 | Jordan ....................... | 422/64 |
| 4,975,647 A | | 12/1990 | Downer et al. | |
| 5,074,157 A | * | 12/1991 | Marsoner et al. .......... | 73/864.81 |
| 5,351,563 A | | 10/1994 | Karpf et al. | |
| 5,384,028 A | | 1/1995 | Ito | |
| 5,658,531 A | * | 8/1997 | Cope et al. ................. | 422/410 |
| 5,690,893 A | | 11/1997 | Ozawa et al. | |
| 6,001,228 A | | 12/1999 | Huber et al. | |
| 6,066,243 A | | 5/2000 | Anderson et al. | |
| 6,368,478 B1 | | 4/2002 | Huber et al. | |
| 6,388,752 B1 | | 5/2002 | Ziegler et al. | |

(Continued)

FOREIGN PATENT DOCUMENTS
DE            19917330  A1  *  10/2000
(Continued)

OTHER PUBLICATIONS
English Machine Translation of DE102005052752A1. Translation Date: Dec. 17, 2011. 34 pages.*
(Continued)

*Primary Examiner* — Bobby Ramdhanie
(74) *Attorney, Agent, or Firm* — Roche Diagnostics Operations, Inc.

(57) ABSTRACT

The invention concerns a sensor cassette that can be inserted into an analyzer comprising a continuous measuring channel for receiving fluidic media and sensory elements for determining chemical and/or physical parameters of the fluidic media. According to the invention the sensor cassette consists of at least two permanently connected but separately manufactured modules which each have a housing and a measuring channel section wherein the measuring channel sections of adjacent modules are connected to the continuous measuring channel by a fluidic coupling and wherein at least one of the connected modules is designed as a sensor module and has a sensor array comprising at least two sensory elements. Furthermore, a memory element is allocated to the sensor cassette on which specific information for the sensor cassette in particular with regard to its construction from the respective modules is stored.

23 Claims, 3 Drawing Sheets

U.S. PATENT DOCUMENTS

| | | |
|---|---|---|
| 6,422,061 B1 | 7/2002 | Sunshine et al. |
| 6,582,964 B1 | 6/2003 | Samsoondar et al. |
| 6,652,810 B1 | 11/2003 | Ziegler |
| 6,896,778 B2 | 5/2005 | Lauks |
| 6,960,466 B2 | 11/2005 | Pamidi et al. |
| 7,171,312 B2 | 1/2007 | Steinthal et al. |
| RE41,946 E | 11/2010 | Anderson et al. |
| 2004/0191124 A1 | 9/2004 | Noetzel et al. |
| 2009/0079963 A1 | 3/2009 | Ermantraut et al. |
| 2009/0132204 A1 | 5/2009 | Bodlaender et al. |

FOREIGN PATENT DOCUMENTS

| | | |
|---|---|---|
| DE | 19917330 B4 | 8/2004 |
| DE | 60023005 T2 | 7/2006 |
| DE | 102005052752 A1 | 5/2007 |
| EP | 0846947 B1 | 6/1998 |
| EP | 1087224 B1 | 4/2004 |
| EP | 1445020 B1 | 8/2004 |
| EP | 1099114 B1 | 11/2004 |
| JP | 8-54399 | 6/1994 |
| WO | 00/62918 A3 | 2/2001 |
| WO | 2008/001279 A3 | 5/2008 |

OTHER PUBLICATIONS

DE102005052752A1. Ermantraut et al. Publication Date: May 10, 2007. 96 pages.*

English Machine Translation of DE19917330. Translation Date: Dec. 17, 2011. 4 pages.*

Hermann et al., "Miniaturized sensor module for in-situ control of waters", Fresenius J Anal Chem (1998), vol. 362, pp. 215-217.

International Preliminary Report on Patentability for PCT Application No. PCT/EP2008/065338; Mailing Date of Jun. 1, 2010; The International Bureau of WIPO; Geneva, Switzerland.

Written Opinion of the International Searching Authority for PCT Application No. PCT/EP2008/065338; English Translation; Mailing Date of Jun. 1, 2010; European Patent Office; Rijswijk, Netherlands.

English Translation of Granted Claims of Japanese Patent No. 3332664.

* cited by examiner

MODULAR SENSOR CASSETTE

This application claims the benefit of U.S. Provisional Patent Application Ser. No. 60/987,446 filed Nov. 13, 2007, entitled "Modular Sensor Cassette" the disclosure of which is hereby incorporated by reference.

BACKGROUND OF THE INVENTION

The invention concerns a sensor cassette that can be inserted into an analyzer and comprises a continuous measuring channel for receiving fluidic media and sensory elements for determining chemical and/or physical parameters of the fluidic media.

Measuring systems for determining several parameters in body fluids are important components of clinically relevant analytical methods. The primary aim is in particular a rapid and precise measurement of so-called emergency parameters.

In medicine, point-of-care testing (abbreviated POCT) refers to diagnostic tests which are not carried out in a central laboratory but rather in the hospital directly in the hospital ward, in intensive care units, in anaesthetics and also in outpatient clinics, in dialysis, in the practices of office-based doctors or during transport of a sick person. POCT has the advantage that results are already available after a short period because, on the one hand, there is no need to transport the samples to a specialized laboratory and, on the other hand, no allowances have to be made for the schedules of the laboratory.

Usually so-called emergency parameters are determined such as e.g., the blood gas values ($O_2$, $CO_2$), the pH value, the electrolyte concentrations ($Li^+$, $Na^+$, $K^+$, $Mg^{++}$, $Ca^{++}$, $Cl^-$), the concentration of metabolites (glucose, lactate, urea, creatinine), the values for the haemoglobin derivatives ($O_2Hb$, HHb, COHb, MetHb) and bilirubin, the haematocrit value, the determination of values for renal function, blood coagulation values, markers for diseases, cardiac and other measurements. However, it is also possible to carry out urine tests, a blood count or to rapidly detect pathogens with the aid of point-of-care methods.

Many point-of-care tests are designed as test strips. However, if it is intended to determine a plurality of parameters simultaneously or in relation to one another, almost completely automated measuring instruments or analyzers are preferably used which are able to simultaneously determine an entire panel of parameters. The determination of a parameter panel is generally understood as the common determination of several individual parameters as part of a measurement. In this connection parameters are preferably determined together which either can easily be determined together because of common principles of measurement (e.g., haemoglobin derivatives based on one measured spectrum, different electrolytes or metabolites by means of analogous electrochemical or optical detection methods) or which are related to one another for a diagnostic evaluation of the analytical results (e.g., concentrations of different cardiac markers for the differential diagnosis of cardiac diseases or concentrations of different haemoglobin derivatives for a differential diagnosis when disorders of gas metabolism are present).

The measurements generally take place in exchangeable measuring chambers which are equipped with electrochemical (electrodes) and/or optical (optodes) sensory elements. In addition, photometric/spectroscopic methods are also used for this in which the optical properties of the sample to be determined or a color reaction is used for the detection. In this case there are special regions in the sample channel which are for example configured as optical cuvettes (optical measuring windows) which can also be regarded as sensory elements in the sense of this application.

The present invention especially concerns those devices in which the measuring chamber is in the form of a measuring channel in which the medium to be examined such as blood is introduced. As a result the medium to be examined comes into contact with the sensory elements in this measuring chamber in order to enable the actual measuring process. In this connection it is possible to combine several different sensory elements into groups of sensory elements (sensor arrays) which are arranged in a common housing or on a common carrier.

In this connection a measuring chamber block of an analyzer is known from U.S. Pat. No. 5,074,157 A (Marsoner) which can be extended in a modular manner. The field of application of the apparatus can be enlarged by coupling further modules. In order to ensure the leak-proofness of the joints of the individual modules, the coupling parts of the modules have sealing rings. Branch-off channels lead away from the measuring channel linking the individual measuring chambers to coupling parts of the module, to which coupling parts of further measuring chambers may be attached. As a result the measuring path is extended which enables the parameter panel to be extended as required. In order to ensure that prescribed sample temperatures are maintained, it is proposed that the modules be inserted into a receiving block with thermostat control. The individual modules are detachably connected to one another and the measuring chamber block formed by the modules cannot be inserted into the holder of an analyzer in the form of an exchangeable sensor cassette.

U.S. Pat. No. 6,960,466 A (Pamidi et al.) describes a sensor cassette which contains a number of individual measuring electrodes for determining different 'point-of-care' parameters such as blood gases, electrolyte values and metabolites which are mounted on a common carrier.

The EP 0846947 (Huber et al.) describes a sensor cassette with electrochemical and/or optical sensors in a planar design which are present on a common sensor component.

A disadvantage of the two known embodiments cited last is that different sensory elements which, for example, require different operating conditions (e.g., different operating temperatures), are present on a single carrier part or sensor component. Another disadvantage is also that the entire sensor cassette with all the sensory elements ends up as a reject if a single sensory element is defective. Another disadvantage is that the known cassettes are not very flexible with regard to a reduction or extension of the parameters panels. New solutions would therefore be desirable for more flexible parameter panels.

SUMMARY OF THE INVENTION

It is against the above background that the present invention provides certain unobvious advantages and advancements over the prior art. In particular, the inventors have recognized a need for improvements in modular sensor cassettes.

In accordance with one embodiment of the present invention, a sensor cassette is provided that can be inserted into an analyzer comprising a continuous measuring channel for receiving fluidic media and sensory elements for determining chemical and/or physical parameters of the fluidic media. The sensor cassette consists of at least two permanently connected but separately manufactured modules which each have a housing and a measuring channel section. The measuring channel sections of adjacent modules are connected to the continuous measuring channel by a fluidic coupling. At least one of the connected modules is designed as a sensor module and has a sensor array comprising at least two sensory elements. A memory element is allocated to the sensor cassette on which specific information for the sensor cassette is stored.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
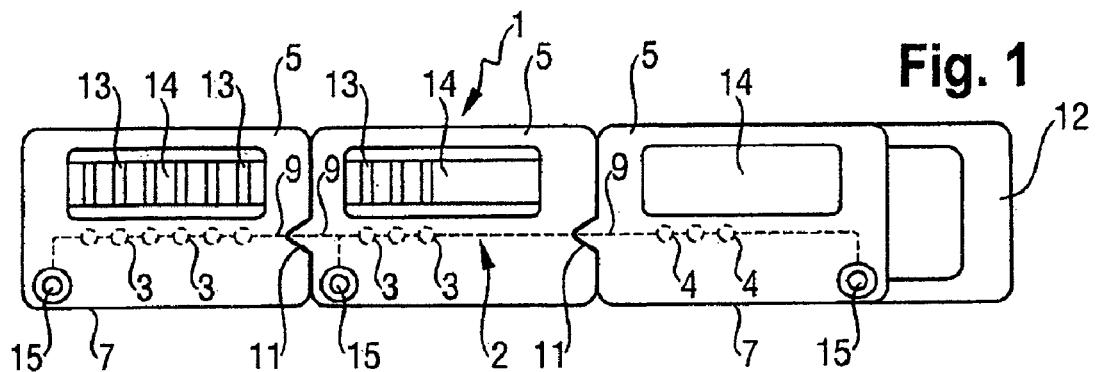
FIG. 1 shows a modular sensor cassette according to an embodiment of the invention comprising three sensor modules in a schematic top-view.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

In accordance with an embodiment of the present invention, a sensor cassette is provided which consists of at least two permanently connected but separately manufactured modules which each have a housing and a measuring channel section, wherein the measuring channel sections of adjacent modules are connected to the continuous measuring channel by a fluidic coupling and wherein at least one of the connected modules is designed as a sensor module and has a sensor array comprising at least two, typically planar, sensory elements. In this case at least this module but typically each module has a plurality of sensory elements.

Furthermore, a memory element is allocated to the sensor cassette according to the invention on which specific information for the sensor cassette in particular with regard to its construction from the respective modules is stored. The common memory element combines the individual modules of the sensor cassette into an integral unit.

This specific information for the sensor cassette is transferred to the analyzer when the sensor cassette according to the invention is inserted into the analyzer, for example by special reading devices that are present in the analyzer. This reading of the specific information for the sensor cassette can be carried out automatically (for example, when the sensor cassette is inserted by means of a reading device integrated into the analyzer) or manually (for example, by entering the information via an input device) and thus transmits the specific information for the sensor cassette to the analyzer.

In principle any device can be used as a memory element which can store information and make it available to an analyzer. Devices are preferably used as memory elements which can automatically make the specific information for the sensor cassette available to a corresponding reading device of the analyzer. Such preferred devices can in particular be electronic memory elements such as memory chips, typically rewritable memory chips or memory cards (e.g., flash memory) or RFID transponders or magnetic strips which transfer the specific information for the sensor cassette to a corresponding reading device in the analyzer when the sensor cassette according to the invention is inserted into the analyzer.

Further possible memory elements are optical codes such as one-dimensional or two-dimensional barcodes which can also be automatically read by means of a barcode scanner.

Furthermore, it is also possible to provide a manual input of the specific information for the sensor cassette in addition to these automated transfer methods, for example such information can be manually entered via an input unit (keyboard) of the analyzer.

In accordance with one embodiment of the present invention, a memory element which contains specific information for the respective sensor cassette is allocated to each sensor cassette according to the invention. This allocation is typically achieved in that the memory element is permanently connected to the sensor cassette in order to ensure an unequivocal allocation. This can for example be achieved by affixing the memory element on the sensor cassette or integrating it into the sensor cassette, for example by gluing on a memory element or incorporating a memory element into the sensor cassette when the latter is assembled. In principle it is also possible to arrange the memory element separately from the sensor cassette but in these cases it must be ensured by other measures, for example, by means of identical codes (e.g., number codes) on the sensor cassette and memory element that the allocation of the sensor cassette and memory element, is unequivocal in order to allocate the correct specific information to the respective sensor cassette.

Specific information for the respective sensor cassette can in general be regarded as all information which describes at least the manner in which the sensor cassette is constructed from the individual modules.

Such information which describes the modular construction of the sensor cassette is for example information about the type of modules used (e.g., sensor module or dummy module; possibly also further information about the type of module, e.g., electrochemical, optical or photometric/spectroscopic measuring module, or the use of the measuring module, e.g., blood gas module, electrolyte module, metabolite module, oximetry module) and information about the arrangement or position of the individual modules within the sensor cassette, for example in which order the individual modules are arranged along the continuous measuring channel.

In a typical embodiment, the specific information for the respective sensor cassette additionally comprises information which describes the manner in which the individual sensory elements (or also vacant regions within the module) are arranged in the respective modules and/or their use and actuation.

Such information which describe the construction and use of the individual modules is for example information about the arrangement, actuation and/or use of the individual sensory elements within the respective module.

In the case of electrochemical sensor modules this can for example be information which describes the arrangement and/or assignment of the individual (electrical) contact points within a tapping region/window of the sensor module and for example described whether such a contact point is connected and to which electrochemical sensor element such a contact point is connected and how it should be used.

In the case of optical sensor modules this can for example be information which describes the arrangement and/or assignment of the individual signal detecting regions within a tapping region/window of the sensor module and for example describes whether such a signal detecting region is connected and to which optical sensory element such a signal detecting region is connected and how it should be used.

In the case of photometric/spectroscopic sensor modules this can for example be information which describes the arrangement of individual optical measuring windows or cuvettes within the measuring channel and/or their use within the respective module.

In addition to this information about the type and manner in which the individual sensory elements are arranged in the respective modules and/or their use and actuation, it can also encompass module-specific information which describes the arrangement and use of individual fluidic connections within the respective module.

Thus, for example, information may be included that describes the type and use of the individual fluidic connections (e.g., fluid connections of the measuring channel (inlet connection of the sensor cassette, outlet connection of the sensor cassette, connections between the individual modules) or fluidic side connections or auxiliary connections (e.g., for supplying the reference electrolyte in the case of electrochemical measuring modules or for supplying reagents required for the analyte determination) or also vacant or dummy connections (e.g., in the case of dummy modules)).

Furthermore, module-specific information may also be included which describes the arrangement and use of certain thermal contact zones within the respective module.

Thus, for example, information may be included about the respective modules which describes the actuation of the individual thermal contact zones by the analyzer, for example information about which thermal contact zone should be thermostatted to which temperature. Alternatively there may also be temperature control devices within the module itself. In these cases information on the respective modules may be included which describes the arrangement of the electrical contact points on the module which are necessary for their actuation and/or their corresponding use.

Furthermore, module-specific information may also be included which describes the arrangement and use of certain fluidic control elements (for example pumps or valves) within the respective module.

Thus, for example, information on the respective modules may be included which describe the use and actuation of the individual fluid control elements by actuators present on the analyzer or module.

This information addressing the respective module is typically at least partially stored on the memory element and can thus be transmitted to the analyzer together with the specific information for the sensor cassette. Alternatively, it is also possible that all or a part of this module-related information is already deposited in a memory of the analyzer such that with knowledge of the information which is contained at least in the memory element and transmitted from this to the analyzer which describes the modular construction of the sensor cassette, it is possible to appropriately link this information together and thus the information necessary for the correct operation of the sensor cassette is available in the analyzer.

In yet another embodiment of the present invention, the specific information for the respective sensor cassette additionally includes information which describes the type of the individual sensory elements and/or their use and actuation.

Such information, for example, includes all information which is necessary to operate the sensory element and/or is used to determine the parameters that are to be determined with the sensory element. Such information is often provided as a standard with exchangeable sensory elements in the form of stored data and comprises, for example, information about the type of sensory element, production information (e.g., batch number), response curve data and/or calibration information or shelf life information (e.g., life time, expiry date, number of possible measurements) of the respective sensory element.

This information addressing the respective sensory element is typically at least partially stored on the memory element and can thus be transmitted to the analyzer together with the specific information for the sensor cassette and optionally also together with further information on the respective module. Alternatively it is also possible that all or only some of this information related to the respective sensory element is already deposited in a memory of the analyzer so that with knowledge of at least the information contained in the memory element and transmitted from this element to the analyzer which describes the modular construction of the sensor cassette (and optionally also information relating to the respective module), it is possible to appropriately link this information and thus information necessary for the correct operation of the sensor cassette is available in the analyzer.

The cassette according to the invention can consist of at least one sensor module and at least one dummy module which apart from the absence of sensory elements is essentially constructed in the same way as the respective sensor module. Hence the dummy module differs from the sensor module in that it has no sensory elements but otherwise has an essentially identical configuration and, for example, has fluidic and electrical connections at similar positions to a sensor module. The external dimensions of the sensor cassette can thus be kept constant.

The cassettes composed of different modules which are used in one type of analyzer particularly advantageously have compatible dimensions and connecting zones. The modular construction ensures a high flexibility. For example new parameters and parameter panels can be developed after the analyzer has been launched on the market without having to retrofit the hardware of the instruments that are already on the market. Furthermore, different modules which can determine different parameters or parameter panels can be assembled in different configurations thus making it possible to offer a user in a simple manner different sensor cassettes adapted to his needs. This modular construction can considerably reduce the manufacturing costs of such different sensor cassettes. Furthermore, in order to determine the same parameter it is also possible to use sensor modules comprising different sensory elements for determining this parameter which, for example, are based on different sensory principles or can cover different concentration ranges of an analyte.

As an alternative to sample input by a device located in the analyzer, sample input can also be carried out by a special module (sample input module) connected to the modular cassette.

A sensor module of a sensor cassette according to the invention, for example, consists of:
  a) a carrier member i.e., a sensor component, on which a sensory element or a number of sensory elements (sensor array) are applied;
  b) a cover member in which a continuous measuring channel or measuring channel section is formed which is intended for the passage of fluidic media;
  c) optionally a sealing element for sealing the measuring channel, where the sealing element is present between the carrier member and the cover member or is molded onto the cover member;
  d) a first opening at one end of the measuring channel for connection to a further module;
  e) a second opening at the other end of the measuring channel for connection to an analyzer or a further module.

The sensor component and the cover member are connected for example:
  with a sealing element;
  by gluing; and/or
  by welding (thermal or by ultrasound).

Further sealing elements may be located at the connecting points of the measuring channel sections of the individual modules or the seal is made by welding. The modules can be firmly held together by a mechanical snap lock or welded or bonded joint. Holding the modules firmly together is in particular understood to mean that the individual modules are connected during the manufacture of the sensor cassette in such a manner that they cannot be separated by the user of the sensor cassette by simple means and typically not without destroying the sensor cassette. Thus for the user the modularly constructed sensor cassette constitutes a single component (consumable) to be inserted into the analyzer.

The modular sensor cassette has at least two fluidic connecting points with the analyzer which serve as an inlet and outlet for sample media and functional fluids (e.g., calibration, quality control and washing fluids) and optionally additional fluidic connecting points with the analyzer for auxiliary fluids (e.g., inner electrolyte for reference electrodes or reagents).

In principle the sensory elements for the individual parameter values to be determined can be distributed over various sensor modules. However, there is typically in each case one separate sensor module for each of the parameter groups blood gases, electrolytes, metabolites, etc., or also other parameter panels.

There can be several variants of individual modules. Thus, for example, a first variant of a module for determining electrolyte values contains sensory elements for measuring the complete electrolyte panel ($Li^+$, $Na^+$, $K^+$, $Ca^{2+}$, $Cl^-$, $Mg^{2+}$). A second variant contains for example sensory elements for measuring the most frequently required electrolyte panel ($Na^+$, $K^+$, $Ca^{2+}$, $Cl^-$).

Similarly a first variant of the module for determining metabolite values contains sensory elements for measuring a broad metabolite panel (glucose, lactate, urea, creatinine). A second variant of the module contains sensory elements for measuring the most frequently required metabolites (glucose, lactate).

This has the advantage that only those sensory elements have to be produced in the factory which are also actually used. In particular, when manufacturing sensor elements which consist of different materials and involve a large number of production steps such as in particular chemical sensor elements, the reject rates are usually high when all sensory elements are integrated into a single sensor component. The manufacture of a sensory element is usually associated with a certain reject rate. The reject rate increases accordingly when several sensory elements are manufactured on a single sensor component. If a sensor cassette comprises a large number of different parameters, the manufacture and assembly of many sensor components each having one sensory element is also complicated. Thus, it has proven to be particularly advantageous to combine sensory elements into groups of sensory elements on the fewest possible sensor components. In this connection it is particularly advantageous when sensory elements having similar structures and which can be manufactured using identical manufacturing steps and manufacturing processes such as, e.g., the group of blood gas electrodes, the group of ion-selective electrodes, the group of amperometric biosensors, are each manufactured on one substrate. This applies similarly to optical sensors. Such arrangements for optical sensors are for example described in U.S. Pat. No. 5,351,563 or U.S. Pat. No. 6,652,810.

Finally sensor modules for photometric/spectroscopic analytical methods may also be provided. Such sensor modules contain special regions within the sample channel (or which are at least fluidically connected to this sample channel and are for example located in a side channel) which are configured as optical cuvettes (optical measuring windows) which can also be regarded as sensory elements in the sense of this application. Examples of such detection methods and sensory principles are the determination of haemoglobin derivatives and bilirubin or photometric HbA1c methods. Examples of arrangements for this are described among others in EP 1 445 020 A1, U.S. Pat. No. 6,582,964 or U.S. Pat. No. 6,388,752.

Furthermore, it is possible to add reagents to a module by means of further connecting points in order to trigger a detection reaction, for example a color reaction and determine the corresponding parameters photometrically. Examples are photometric HbA1c methods of determination.

Further sensor modules can contain sensory elements based on immunological methods, for example for determining certain cardiac markers such as NTproBNP or troponin. In the case of such immunological detection methods it is necessary to add further reagents (e.g., antibodies, labels, washing solutions) for the analyte determination which can be brought into the respective sensor module by additional fluidic connections (in the sense of fluidic auxiliary connections) or are already present in this sensor module. The sensory detection principles can in this case be photometric or spectroscopic detection methods (e.g., detection by means of gold-labelled or dye-labelled antibodies), but other detection methods are also basically conceivable.

In addition, a module for determining coagulation parameters can also be provided. Also when determining coagulation parameters which are usually based on enzymatic reactions, it is necessary to add further reagents (e.g., labelled specific substrates) for the analyte determination which can be brought into the respective sensor module by additional fluidic connections (in the sense of fluidic auxiliary connections) or are already present in this sensor module. The sensory detection principles can in this case be photometric or spectroscopic detection methods (e.g., detection of colored reaction products of an enzymatic reaction), but other detection methods (e.g., detection of electrochemically active reaction products of an enzymatic reaction by means of electrochemical detection methods) are also basically conceivable.

The sensor cassette 1 shown schematically in FIG. 1 can be inserted into the holder of an analyzer which is not shown in further detail and has a continuous measuring channel 2 (shown by the dashed line) which is used to hold fluidic media such as, for example, sample liquids, calibration, quality control and washing media. Sensory elements 3, 4 for determining chemical and/or physical parameters of the fluidic media are arranged in the sensor cassette 1. According to FIG. 1, the sensor cassette 1 consists of three permanently connected modules 5 which outwardly are constructed in essentially the same manner and which each have measuring channel sections 9 in a housing 7 where the measuring channel sections of adjacent modules are connected to the continuous measuring channel 2 by means of a fluidic coupling 11. In the example shown, each of the modules 5 is designed as a sensor module for different types of sensory elements where the first two modules have electrochemical sensors 3 and the last module 5 with the grip element 12 for example has optical sensors 4.

In the modules 5 containing the electrochemical sensors 3, electrical contact points 13 are indicated which can be contacted through a window 14 in the module 5 by corresponding contact pins of the analyzer. In this connection the facts essentially correspond to those of EP 0 846 947 B1 cited above. The fluid connections of the sensor cassette 1 to the analyzer are referred to as 15. In the last module 5 with the grip element 12 which contains optical sensors 4, signal tapping regions are formed within the window 14 (not explicitly shown) which are each connected to an optical sensor 4 and transmit its respective response to the analyzer for the parameter determination.

The comparison of the embodiment variants of the sensor cassette 1 according to FIGS. 1 to 4 shows that the outer dimensions of the individual variants are compatible despite the different sensor modules which also applies in particular to the shape and position of the fluid connections 15. In the case shown in FIG. 1, the fluidic connections 15 of the two outer modules are configured as a sensor cassette inlet and outlet of the continuous measuring channel 2 which enable a fluidic connection to the analyzer for the purpose of introducing sample liquids and/or functional fluids. The fluidic connection 15 of the middle sensor module can in this case serve as a fluidic side connection or auxiliary connection (e.g., for feeding in the reference electrolyte in the case of electrochemical measuring modules or for feeding in reagents required for the analyte determination).

Figure 2:
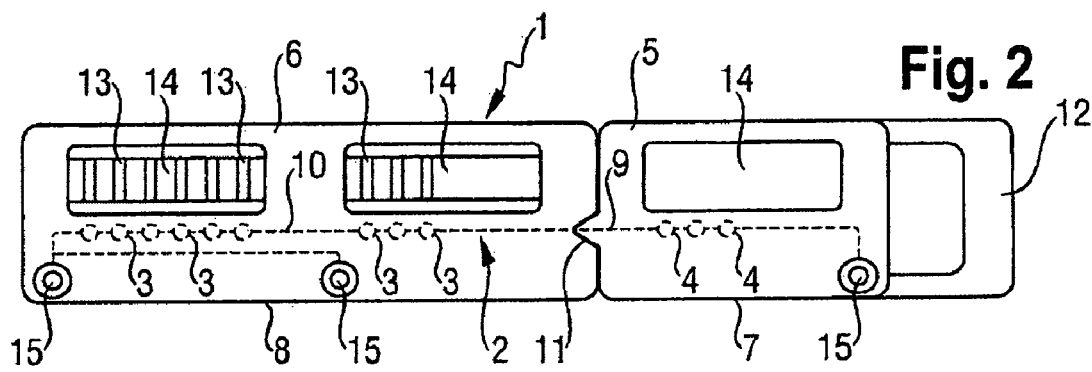
FIG. 2 shows a variant of the sensor cassette according to FIG. 1 comprising two sensor modules combined into a double module.

Thus, for example, according to the embodiment variant of FIG. 2, two single modules are combined to form a longer module 6 with a housing 8 where module 6 has twice the length of module 5. In the arrangement shown here one of the two fluidic connections 15 of the module 6 is configured as a sensor cassette inlet or outlet of the continuous measuring channel 2 whereas the other fluid connection is configured in this case as a fluidic side connection or auxiliary connection (e.g., for feeding in the reference electrolyte in the case of electrochemical measuring modules or for feeding in reagents required for the analyte determination).

One module can in principle also contain sensory elements which are based on different detection principles. For example, in FIG. 2 the module shown on the left can contain electrochemical sensory elements in its left region and could contain other sensory elements such as optical sensory elements in the right region.

Figure 3:
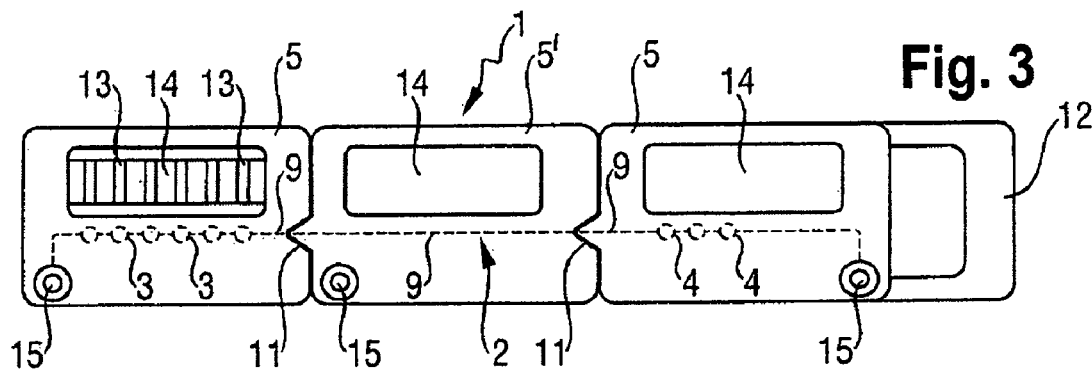
FIG. 3 shows a variant of the sensor cassette according to FIG. 1 in which one sensor module is replaced by a dummy module.

Furthermore, according to the embodiment variant in FIG. 3, the sensor cassette 1 has two sensor modules 5 and (in the middle) a dummy module 5' which, apart from the absence of sensory elements, essentially corresponds to the sensor modules 5. In this case the fluidic connection 15 of the dummy module 5' is configured as a vacant connection or dummy connection.

Figure 4:
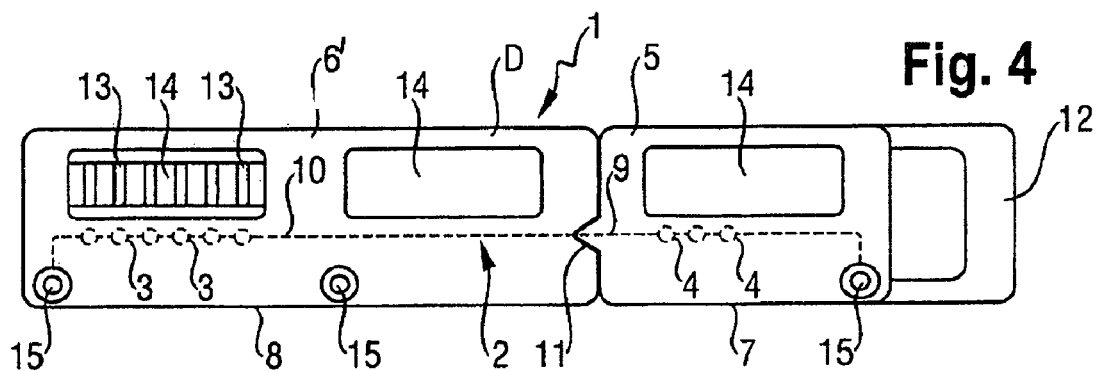
FIG. 4 shows a variant of the sensor cassette according to FIG. 2 in which a region D free of sensor elements is implemented in a double module.

As shown in FIG. 4, it is also possible to provide a module 6' in the sensor cassette 1 which has a sensor array comprising sensory units 3 and a free region D which is free of sensory elements. As a result of this design the same outer dimensions can be achieved even when it is fitted with different sensory elements. The dummy module 5' (FIG. 3) or the free region D of the module 6' (FIG. 4) can have a fluid connection 15 which is configured as a vacant connection.

According to the invention the sensor modules 5, 6 and the dummy modules 5', 6' of a sensor cassette 1 collectively have dimensions and fluid connections 15 which correspond to the holder of the analyzer. The same also applies to the electrical contact points 13 or other signal-tapping regions within the window 14.

Figure 5:
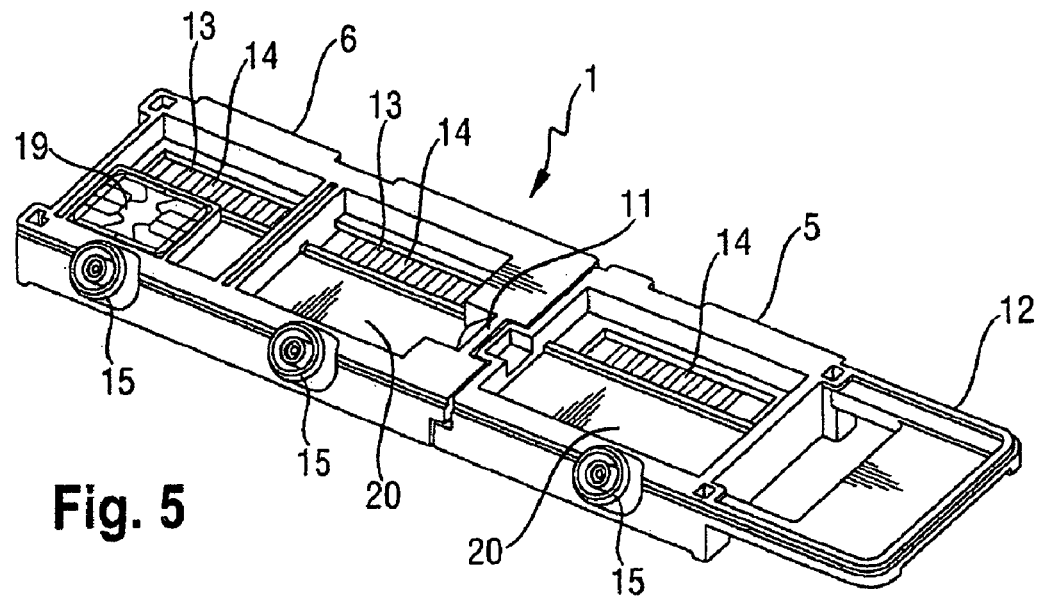
FIG. 5 shows a concrete embodiment example of a modular sensor cassette in a three-dimensional diagram.
Figure 6:
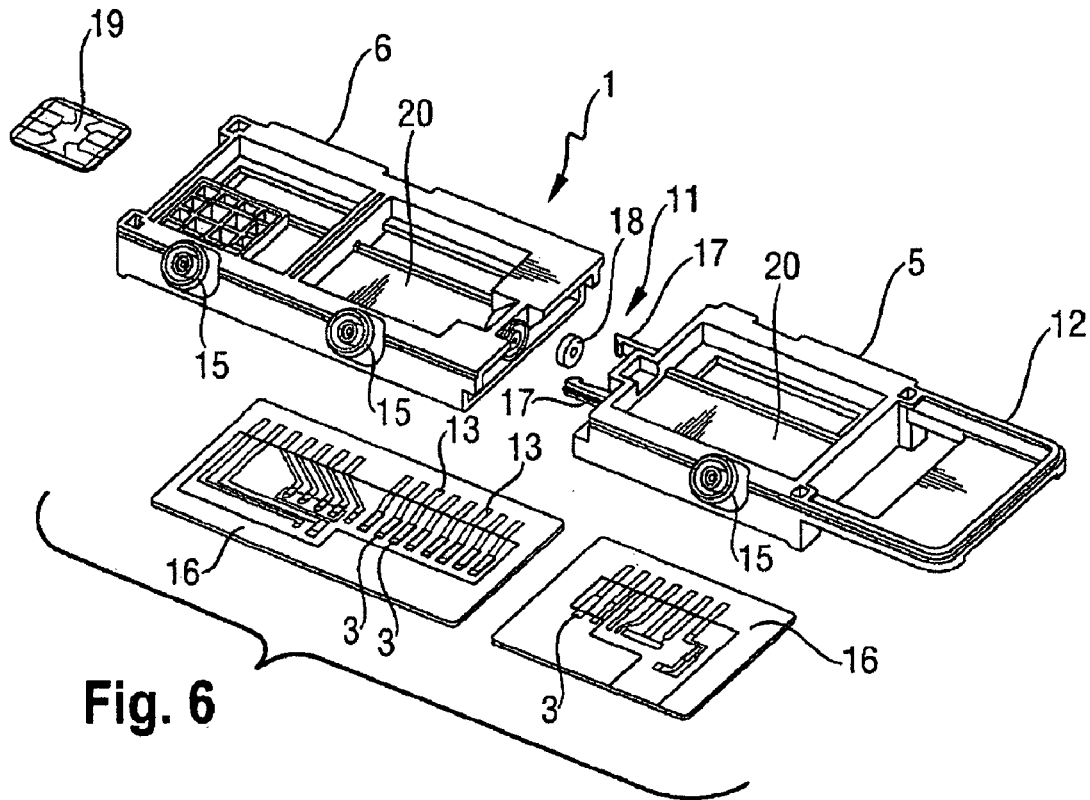
FIG. 6 shows a modular sensor cassette according to FIG. 5 in an exploded view.

A concrete embodiment example of a modular sensor cassette 1 is shown in FIGS. 5 and 6 which consists of a single module 5 (in this case with a permanently connected grip part 12) and a double module 6 containing two fluid connections 15. It can be seen in particular from FIG. 6 that a number of electrochemical sensor elements 3 are mounted on a carrier part 16, the sensor elements being connected to the contact points 13 by conductor paths. The electrical contacts are tapped by the analyzer through the window 14 of the modules 5, 6.

The individual modules 5, 6 of the sensor cassette 1 are connected together by a permanent mechanical snap lock, for example by means of locking elements 17, with a seal 18 being placed in between. The permanent connection can also be made by a welded joint or by a bonded joint.

A memory element 19 on which specific information for the sensor cassette 1 is stored and in particular with regard to how it is constructed from the respective modules 5, 6 which is automatically read after the sensor cassette 1 is inserted into the analyzer, is arranged as a memory chip on one of the modules 5, 6 of the sensor cassette 1.

The carrier part 16 (for example its rear side) can serve as a thermal contact zone which allows the individual modules 5, 6 in the analyzer to be thermostatted at a different operating temperature. As shown in FIG. 6, the thermal contact zones of adjacent modules 5, 6 of the sensor cassette 1 can be thermally decoupled (e.g., by an appropriate spacing between the carrier parts 16 or by temperature-insulating materials).

The sensor modules 5, 6 can have optical passage zones for excitation and measuring radiation if optical sensors 4 are present in the module. In addition, optical windows (cuvettes) for transmission or reflection measurements can be provided. This for example allows haemoglobin values to be determined by means of spectroscopic methods.

The dummy modules 5', 6' can also contain thermal contact zones for preheating or cooling the sample and functional fluids in order to for example at least partially preheat them to an operating temperature required in subsequent sensor modules. Alternatively, temperature control devices can also be located within the modules themselves which for example are actuated by the analyzer by an appropriate electrical contacting.

The sensor modules 5, 6 can thus be thermostatted at different operating temperatures, e.g., the sensors of a first module can be operated at body temperature (e.g., blood gas sensors at −37° C.) and the sensors of a second module can be operated at a lower temperature (e.g., metabolite or electrolyte sensors at 30° C.).

As a result a higher operating stability is achievable for the sensitive biochemical sensors.

It is particularly advantageous for operating at different temperatures when the sensor modules 5, 6 are at least partially thermally decoupled at the contact points, for example by means of materials having a low heat conduction.

Individual modules of the sensor cassettes can also have regions containing fluidic elements or functionalities integrated into the fluid paths which for example comprise valve functions or pump functions. These act on the fluid flowing through the fluid paths by means of appropriate actuators. Thus, for example, valves can be used which make a through connection or close the fluid paths. On the other hand, pumps can be integrated into the individual modules to transport the fluid. In this connection it is not absolutely necessary that all components of the fluidic elements or functionalities are present in the module. Certain components of these fluidic elements or functionalities can also be located in the analyzer and then engage with corresponding partial elements in the modules so that acting in cooperation they have an effect on the fluid. Examples of this are peristaltic pumps with a rotor in the analyzer and a tube in the module or stop valves with plungers arranged in the analyzer and corresponding squeezable sections of tubes arranged in the module.

The modular sensor cassette is typically assembled in the factory and packaged ready-for-use by the user in suitable containers.

In order that the invention may be more readily understood, reference is made to the following examples, which are intended to illustrate the invention, but not limit the scope thereof.

Example 1

The modular sensor cassette 1 for determining blood values (see FIGS. 5 and 6) is implemented with two sensor modules 5, 6 which are inseparably connected in the factory by a snap connection. The first module 5 of the sensor cassette contains sensory elements for determining the blood gas parameters ($pO_2$, $pCO_2$), the pH value and the haematocrit. The second module 6 contains sensory elements for determining metabolite values (glucose, lactate) and electrolyte concentrations ($Na^+$, $K^+$, $Ca^{2+}$, $Cl^-$). Module 6 additionally contains a reference electrode (shown here by the two conductor paths on the left side which are mounted on the carrier 16 of module 6) which is supplied with a functional fluid (=inner electrolyte liquid) from the analyzer via the right fluidic connection 15 of the module 6.

In this example the sensor modules 5, 6 have different geometric dimensions.

Sealing elements between the carrier parts 16 and the corresponding upper parts of the housing of the respective modules are not explicitly shown in the figures. These sealing elements in conjunction with the respective carriers and upper parts of the housing define the fluidic channels and in particular also the measuring channel within the respective modules.

The second module 6 is almost twice as long as the first module 5 (minus the grip part 12). Both modules are operated at different temperatures (37° C. and 30° C.).

Example 2

Figure 7:
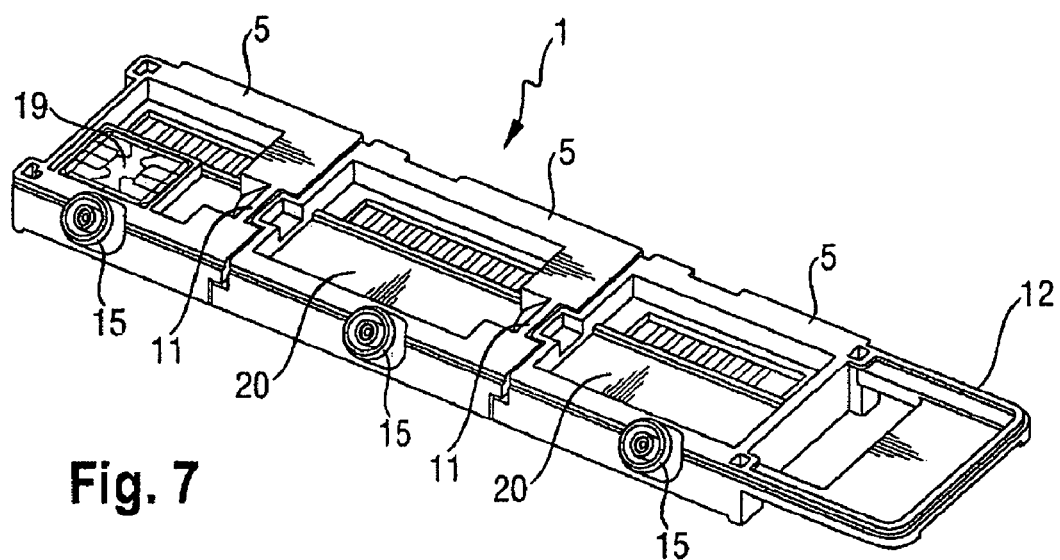
FIG. 7 shows another, concrete embodiment example of a modular sensor cassette in a three-dimensional view.

Alternatively, the second module 6 from Example 1 can be replaced by two short modules 5 (see FIG. 7), one of which contains the electrolyte sensors and the other contains the metabolite sensors. As a result, one obtains a modular sensor cassette 1 according to an embodiment of the invention comprising a blood gas module (with grip part 12), an electrolyte module (in the middle) and a metabolite module. The position and use of the fluidic connections 15 is only shown schematically here.

In principle the type and arrangement of the modules within the sensor cassette is not subject to any restrictions. Thus, in principle, further modules can be inserted in addition to sensor modules and dummy modules, which can assume special functions. Thus, for example, special sample input modules can be used which have special devices (e.g., connections for capillaries or syringes) by means of which the sample liquid to be examined can be introduced into the sensor cassette. Furthermore, special sample input and/or sample output modules can also be used which are arranged at the end of the sensor cassette and transport the sample liquid or other functional fluids to or from the other modules arranged in the middle of the sensor cassette. Such special sample input and/or sample output modules can thus serve as fluidic points of contact with the analyzer which can be used universally and connect the sample channel of the sensor cassette to corresponding fluidics in the analyzer so that all further (inner) modules can in principle be configured with the same dimensions and connections by which means they can in principle be combined in an unlimited manner.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A sensor cassette that can be inserted into a holder of an analyzer, the sensor cassette comprising:
    a continuous measuring channel for receiving fluidic media and sensory elements for determining at least one of: chemical parameters of the fluidic media physical parameters of the fluidic media;
    at least two permanently coupled but separately manufactured modules, the modules each having a housing and a measuring channel section, wherein:
        the measuring channel sections of adjacent modules are permanently coupled to the continuous measuring channel by a fluidic coupling;
        at least one of the modules is designed as a sensor module and has a sensor array comprising at least two sensory elements;
        the modules collectively define the sensor cassette, the sensor cassette having dimensions that correspond to dimensions of the holder of the analyzer; and
        fluid connections of the sensor cassette align with corresponding fluid connections of the holder of the analyzer when the sensor cassette is inserted into the holder of the analyzer; and
    a memory element on the sensor cassette with information stored thereon, wherein, when the sensor cassette is inserted into the holder of the analyzer, the information is read out by the analyzer and instructs a processor of the analyzer to configure the analyzer for interaction with the sensor cassette.

2. The sensor cassette according to claim 1, wherein at least one of the modules is a dummy module which, apart from the absence of sensory elements, is constructed in essentially the same manner as the respective sensor module.

3. The sensor cassette according to claim 1, wherein at least one sensor module includes a sensor array comprising at least two sensory elements and a free region which is free of sensory elements.

4. The sensor cassette according to claim 1, wherein at least two of the modules of the sensor cassette are coupled together by a permanent mechanical snap connection.

5. The sensor cassette according to claim 1, wherein at least two of the modules of the sensor cassette are permanently coupled together by at least one of: locking elements, a welded joint, and a bonded joint.

6. The sensor cassette according to claim 1, wherein the modules have one or more thermal contact zones.

7. The sensor cassette according to claim 6, wherein the thermal contact zones are configured such that the modules can be set to different operating temperatures.

8. The sensor cassette according to claim 6, wherein the thermal contact zones of adjacent modules of the sensor cassette are thermally decoupled.

9. The sensor cassette according to claim 1, wherein a module at the edge of the sensor cassette has a grip part.

10. The sensor cassette according to claim 1, wherein the information stored on the memory element configures the analyzer by describing the type of modules used and their arrangement or position within the sensor cassette.

11. The sensor cassette according to claim 1, wherein the information stored on the memory element configures the analyzer by describing the manner in which the individual sensory elements or free regions are arranged within the respective modules and/or instructions on the use of the modules for the analyzer.

12. The sensor cassette according to claim 11, wherein the information stored on the memory element further configures the analyzer by describing the arrangement and/or use of electrical contact points or other signal transferring regions, fluidic connections, thermal contact zones and/or fluidic control elements within the individual modules.

13. The sensor cassette according to claim 1, wherein the information stored on the memory element configures the analyzer by describing the type of individual sensory elements and/or their use and actuation.

14. The sensor cassette according to claim 13, wherein the information stored on the memory element further configures the analyzer by describing includes production information, response curve data and/or calibration information or shelf life information of the respective sensory element.

15. The sensor cassette according to claim 1, wherein the memory element is an electronic memory element.

16. The sensor cassette according to claim 1, wherein the memory element is selected from the group consisting of memory chips, memory cards, RFID transponders, magnetic strips, optical codes, and combinations thereof.

17. The sensor cassette according to claim 16, wherein the optical code is a one-dimensional or two-dimensional bar code.

18. The sensor cassette according to claim 1, wherein the memory element is permanently connected to the sensor cassette.

19. The sensor cassette according to claim 18, wherein the memory element is permanently coupled to the sensor cassette by a select one of: mounting the memory element on the sensor cassette, or incorporating a memory element into the sensor cassette during its assembly.

20. The sensor cassette according to claim 1, wherein the sensor elements and electrical contact points of at least one module are arranged on a carrier part.

21. The sensor cassette according to claim 20, wherein the modules have one or more thermal contact zones defined by the carrier part and the thermal contact zones each include a temperature control device operated by the analyzer.

22. The sensor cassette according to claim 1, wherein at least one of the modules comprises a sensor array having at least two sensory elements and corresponding electrical contact points, wherein the electrical contact points align with corresponding electrical contact points in the analyzer when the sensor cassette is inserted into the holder of the analyzer.

23. A sensor cassette that can be inserted into a holder of an analyzer, the sensor cassette comprising:
    a continuous measuring channel for receiving fluidic media and sensory elements for determining at least one of: chemical parameters of the fluidic media and physical parameters of the fluidic media; and
    at least two inseparably connected but separately manufactured modules, the modules each having a housing and a measuring channel section, wherein:
        the measuring channel sections of adjacent modules are permanently coupled to the continuous measuring channel by a fluidic coupling;
        at least one of the modules is designed as a sensor module and has a sensor array comprising at least two sensory elements;
        the modules collectively define the sensor cassette, the sensor cassette having dimensions that correspond to dimensions of the holder of the analyzer; and
        fluid connections of the sensor cassette align with corresponding fluid connections of the holder of the analyzer when the sensor cassette is inserted into the holder of the analyzer; and
    a memory element on the sensor cassette with information stored thereon, wherein, when the sensor cassette is inserted into the holder of the analyzer, the information is read out by the analyzer and instructs a processor of the analyzer to configure the analyzer for interaction with the sensor cassette.

* * * * *